(12) United States Patent
Shekh Yosef

(10) Patent No.: US 12,733,990 B2
(45) Date of Patent: Sep. 15, 2026

(54) ELECTROMAGNETIC AND CAMERA-GUIDED NAVIGATION

(71) Applicant: Covidien LP, Mansfield, MA (US)

(72) Inventor: Lana Shekh Yosef, Tel Aviv District (IL)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/761,515

(22) Filed: Jul. 2, 2024

(65) Prior Publication Data

US 2025/0072978 A1 Mar. 6, 2025

Related U.S. Application Data

(60) Provisional application No. 63/534,966, filed on Aug. 28, 2023.

(51) Int. Cl.

| | |
|---|---|
| ***A61B 34/20*** | (2016.01) |
| ***A61B 1/00*** | (2006.01) |
| ***A61B 1/018*** | (2006.01) |
| ***A61B 1/04*** | (2006.01) |
| ***A61B 10/04*** | (2006.01) |

(Continued)

(52) U.S. Cl.

CPC .......... *A61B 34/20* (2016.02); *A61B 1/00009* (2013.01); *A61B 1/0005* (2013.01); *A61B 1/018* (2013.01); *A61B 1/04* (2013.01); *A61B 10/04* (2013.01); *G06T 15/205* (2013.01); *A61B 2034/2051* (2016.02); *A61B 2034/2065* (2016.02); *A61B 2090/367* (2016.02); *G06T 2210/41* (2013.01)

(58) Field of Classification Search

CPC .............. A61B 34/20; A61B 2090/367; A61B 2090/364; A61B 2034/2051; A61B 1/00009; A61B 1/0005; A61B 1/018; A61B 1/04; A61B 10/04; A61B 2034/2065; G06T 15/205; G06T 2210/04

See application file for complete search history.

(56) References Cited

U.S. PATENT DOCUMENTS

| | | | |
|---|---|---|---|
| 10,796,432 | B2 | 10/2020 | Mintz et al. |
| 11,172,184 | B2 | 11/2021 | Komp et al. |

(Continued)

OTHER PUBLICATIONS

PCT Search Report and Written Opinion issued in PCT Application No. PCT/IB2024/058168 dated Nov. 5, 2024.

*Primary Examiner* — Amelie R Davis

(74) *Attorney, Agent, or Firm* — Weber Rosselli & Cannon LLP

(57) ABSTRACT

A system for performing a surgical procedure includes a catheter with a camera configured to capture images of a patient's anatomy, a biopsy tool, and a workstation operably coupled to the catheter and the biopsy tool, the workstation including a memory and a processor, the memory storing instructions, which when executed by the processor cause the processor to receive a plurality of images captured by the camera at a plurality of locations in a patient's anatomy, identify coordinates of the catheter at each respective location at which each received image of the plurality of images was captured, identify coordinates of the biopsy tool within the patient's anatomy, identify an image of the plurality of received images having coordinates corresponding to the identified coordinates of the biopsy tool, and display the identified image on a user interface.

14 Claims, 9 Drawing Sheets

(51) Int. Cl.
*A61B 90/00* (2016.01)
*G06T 15/20* (2011.01)

(56) References Cited

U.S. PATENT DOCUMENTS

| | | | |
|---|---|---|---|
| 11,553,968 | B2 | 1/2023 | Hunter et al. |
| 2018/0279852 | A1 | 10/2018 | Rafii-Tari et al. |
| 2019/0105113 | A1* | 4/2019 | Popovic ............. A61B 1/00087 |
| 2020/0195903 | A1* | 6/2020 | Komp .................... H04N 23/20 |
| 2020/0297444 | A1 | 9/2020 | Camarillo et al. |
| 2021/0369355 | A1 | 12/2021 | Masaki et al. |
| 2021/0393344 | A1 | 12/2021 | Graetzel et al. |
| 2022/0202500 | A1 | 6/2022 | Ninni et al. |

* cited by examiner

ELECTROMAGNETIC AND CAMERA-GUIDED NAVIGATION

CROSS-REFERENCE TO RELATED APPLICATIONS

This application claims the benefit of U.S. Provisional Patent Application Ser. No. 63/534,966, filed Aug. 28, 2023, the entire content of which is incorporated herein by reference.

TECHNICAL FIELD

The present disclosure relates to the field of navigating medical devices to a target area, and particularly to visualizing the navigation of medical devices to a target area.

BACKGROUND

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., for example, without causing damage to other organs or tissue).

For example, an endoscopic approach has proven useful in navigating to areas of interest within a patient. To enable the endoscopic approach endoscopic navigation systems have been developed that use previously acquired MRI data or CT image data to generate a three-dimensional (3D) rendering, model, or volume of the particular body part such as the lungs.

The resulting volume generated from the MRI scan or CT scan is then utilized to create a navigation plan to facilitate the advancement of the endoscope (or other suitable medical device) within the patient anatomy to an area of interest. A locating or tracking system, such as an electromagnetic (EM) tracking system, may be utilized in conjunction with, for example, CT data, to facilitate guidance of the endoscope to the area of interest.

To assist with alignment of a surgical tool with a target, catheters having cameras may be advanced within an extended working channel (EWC) and used to capture images of the area of interest and the target. However, the catheter is often required to be removed from the EWC to permit advancement of a biopsy tool or other medical device within the EWC to obtain a biopsy sample or perform a surgical procedure. As can be appreciated, removal of the catheter from the EWC, or external forces acting upon the EWC, may cause the position of the EWC to shift relative to the target. With the catheter removed from the EWC, visual guidance is not available to ensure proper alignment of the biopsy tool with the target, which may result in inaccurate or incomplete biopsy samples of the target.

SUMMARY

In accordance with the disclosure, a system for performing a surgical procedure includes a catheter with a camera configured to capture images of a patient's anatomy, a biopsy tool, and a workstation operably coupled to the catheter and the biopsy tool, the workstation including a memory and a processor, the memory storing instructions, which when executed by the processor cause the processor to receive a plurality of images captured by the camera at a plurality of locations in a patient's anatomy, identify coordinates of the catheter at each respective location at which each received image of the plurality of images was captured, identify coordinates of the biopsy tool within the patient's anatomy, identify an image of the plurality of received images having coordinates corresponding to the identified coordinates of the biopsy tool, and display the identified image.

In aspects, the system may include an extended working channel configured to receive the catheter and the biopsy tool.

In other aspects, the system may include the memory storing thereon further instructions, which when executed by the processor cause the processor to receive the plurality of images captured by the camera at the plurality of locations when the catheter is advanced within the extended working channel and the biopsy tool is withdrawn from the extended working channel.

In certain aspects, the system may include the memory storing thereon further instructions, which when executed by the processor cause the processor to identify the coordinates of the biopsy tool within the patient's anatomy when the biopsy tool is advanced within the extended working channel and the catheter is withdrawn from the extended working channel.

In other aspects, the system may include the memory storing thereon further instructions, which when executed by the processor cause the processor to generate a 3-dimensional rendering of the patient's anatomy using the plurality of received images.

In aspects, the system may include the memory storing thereon further instructions, which when executed by the processor cause the processor to monitor coordinates of the biopsy tool in real-time as the biopsy tool is caused to be manipulated within the patient's anatomy.

In certain aspects, the system may include the memory storing thereon further instructions, which when executed by the processor cause the processor to update the display identified image in real-time corresponding to the manipulation of the biopsy tool within the patient's anatomy.

In aspects, the system may include the memory storing thereon further instructions, which when executed by the processor cause the processor to generate a radius extending from a center of a target tissue.

In other aspects, the system may include the memory storing further instructions, which when executed by the processor cause the processor to receive the plurality of images captured by the camera at the plurality of locations within extents of the generated claims.

In accordance with another aspect of the disclosure, a system for performing a surgical procedure includes an extended working channel navigable within a body cavity of a patient, a catheter selectively receivable within the extended working channel, the catheter including a camera configured to capture images of a patient's anatomy, a biopsy tool selectively receivable within the extended working channel, and a workstation operably coupled to the catheter and the biopsy tool, the workstation including a memory and a processor, the memory storing instructions, which when executed by the processor cause the processor to receive a plurality of images captured by the camera at a plurality of locations in a patient's anatomy, identify coordinates of the catheter at each respective location at which each received image of the plurality of images was captured, generate, using the received plurality of images, a 3D representation of the patient's anatomy, identify coordinates of the biopsy tool within the patient's anatomy, identify a position within the generated 3D representation corresponding to the identified coordinates of the biopsy tool, and display the 3D representation from a perspective corresponding to the identified coordinates of the biopsy tool.

In aspects, the system may include the memory storing further instructions, which when executed by the processor cause the processor to monitor coordinates of the biopsy tool as the biopsy tool manipulated within the patient's anatomy.

In certain aspects, the system may include the memory storing further instructions, which when executed by the processor cause the processor to update the displayed perspective of the 3D representation corresponding the manipulation of the biopsy tool within the patient's anatomy.

In other aspects, the system may include the memory storing thereon further instructions, which when executed by the processor cause the processor to generate a radius extending from a center of a target tissue.

In certain aspects, the system may include the memory storing further instructions, which when executed by the processor cause the processor to receive the plurality of images captured by the camera at the plurality of locations within extents of the generated radius.

In accordance with another aspect of the disclosure, a method of performing a surgical procedure includes capturing a plurality of images at a plurality of locations within a body cavity of a patient, wherein the plurality of images is captured using a camera disposed on a catheter, identifying coordinates of the catheter at each respective location at which each received image of the plurality of images was captured, withdrawing the catheter from the body cavity of the patient, advancing a biopsy tool into the body cavity of the patient, identifying coordinates of the biopsy tool within the body cavity of the patient, identifying an image of the plurality of received images having coordinates corresponding to the identified coordinates of the biopsy tool, and displaying the identified image.

In aspects, withdrawing the catheter from the body cavity of the patient may include withdrawing the catheter from an extended working channel.

In certain aspects, the method may include monitoring coordinates of the biopsy tool as the biopsy tool is manipulated within the body cavity of the patient.

In other aspects, the method may include updating the displayed identified image corresponding to the manipulation of the biopsy tool within the body cavity of the patient.

In aspects, the method may include generating a radius extending from a center of a target tissue within the body cavity of the patient.

In other aspects, capturing the plurality of images may include capturing the plurality of images at the plurality of locations within extents of the generated radius.

BRIEF DESCRIPTION OF THE DRAWINGS

Various aspects and embodiments of the disclosure are described hereinbelow with references to the drawings, wherein.

DETAILED DESCRIPTION

Figure 1:
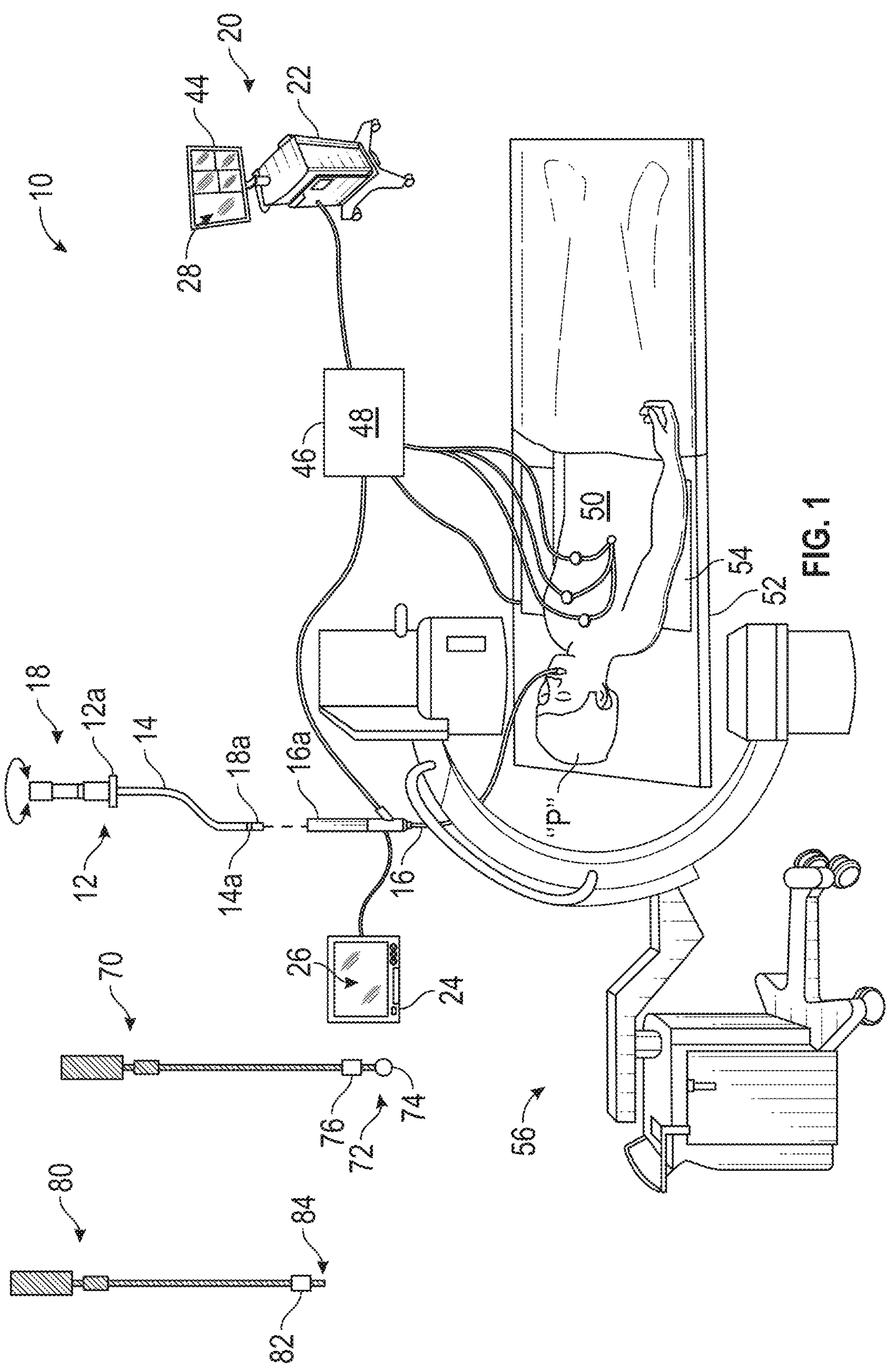
FIG. 1 is a schematic view of a surgical system provided in accordance with the present disclosure.

The present disclosure is directed to a surgical system having an extended working channel (EWC), which may be a smart extended working channel (sEWC) including an electromagnetic (EM) sensor, a locatable guide (LG) selectively receivable within the sEWC, a biopsy tool selectively receivable within the sEWC, and a catheter selectively receivable within the sEWC, wherein a distal portion of the catheter includes a camera. The system includes an electromagnetic navigation (EMN) or tracking system for tracking the location of EM sensors disposed on or within each of the sEWC, the LG, the biopsy tool, and the catheter. In operation, the sEWC is navigated to an area of interest within a body cavity of a patient P. As compared to an EWC, the sEWC includes a separate EM sensor from the EM sensor disposed on the LG. In this manner, the sEWC may be navigated using only the EM sensor disposed on the sEWC, the LG may be advanced within the sEWC and the sEWC may be navigated using the EM sensor disposed on the LG, or the sEWC may be navigated using the camera and/or EM sensor disposed on the catheter.

With the sEWC located at a desired position relative to target tissue within the area of interest where the target tissue is entirely within a field of view of the camera, a plurality of images is captured by the camera disposed on the catheter at a plurality of locations adjacent the target tissue. As can be appreciated, if the LG is used to navigate the sEWC, the LG is withdrawn from the sEWC and the catheter is advanced within the sEWC, and if the sEWC is navigated using its own EM sensor, the catheter is likewise advanced within the sEWC. Using the EM sensor disposed on the catheter, the system identifies coordinates of the catheter within the patient's anatomy at the location where each corresponding image is captured by the camera, and the identified coordinates are assigned to reach a respective image of the plurality of images. The system generates a radius extending from a center of the target tissue, and the plurality of images is obtained within the extents of the radius. As can be appreciated, the catheter is advanced within each navigable airway within extents of the radius and the plurality of images is captured within the extents of the radius.

With the plurality of images captured by the camera within the extents of the radius, the catheter is withdrawn from the sEWC. As can be appreciated, removal of the catheter, or external forces (e.g., for example, tidal breathing), may cause the position of the sEWC to shift. Without visual guidance from the camera disposed on the catheter, it is difficult to ensure that the biopsy tool is positioned at the correct location relative to the target tissue and ensure an accurate biopsy sample of the target tissue is obtained. The system identifies the coordinates of the EM sensor disposed on the biopsy tool, and therefore, the location of the biopsy tool and identifies an image of the plurality of images having coordinates that correlate to the identified coordinates of the biopsy tool. The identified image is displayed on a user interface to provide visual guidance during manipulation of the biopsy tool relative to the target tissue as if the catheter is still within the body cavity of the patient, aiding both alignment of the biopsy tool with the target tissue and accurate sampling of the target tissue. Although generally described as using singular, still-frame images, it is contemplated that the coordinates of the biopsy tool may be monitored in real-time and the displayed images corresponding to the coordinates of the biopsy tool may be updated in real-time, or a video or fly-through view may be displayed on the user interface.

It is envisioned that the system may generate a 3-dimensional (3D) model or representation of the patient's anatomy adjacent to the target tissue using the images captured by the camera disposed on the catheter. In this manner, as the biopsy tool is manipulated relative to the target tissue, the 3D representation is updated in real-time to display a perspective as if the camera is being manipulated. These and other aspects of the present disclosure will be described in further detail hereinbelow. Although generally described with reference to the lung, it is contemplated that the systems and methods described herein may be used with any structure within the patient's body, such as for example, the liver, kidney, prostate, or gynecological.

Turning now to the drawings, FIG. 1 illustrates a system 10 in accordance with the disclosure facilitating navigation of a medical device through a luminal network and to an area of interest. The system 10 includes a catheter guide assembly 12 including an extended working channel (EWC) 14, which may be a smart extended working channel (sEWC) including an electromagnetic (EM) sensor. In one embodiment, the sEWC 14 is inserted into a bronchoscope 16 for access to a luminal network of the patient P. In this manner, the sEWC 14 may be inserted into a working channel of the bronchoscope 16 for navigation through a patient's luminal network, such as for example, the lungs. It is envisioned that the sEWC 14 may itself include imaging capabilities via an integrated camera or optics component (not shown) and therefore, a separate bronchoscope 16 is not strictly required. In embodiments, the sEWC 14 may be selectively locked to the bronchoscope 16 using a bronchoscope adapter **16*a*. In this manner, the bronchoscope adapter 16*a* is configured to permit motion of the sEWC 14 relative to the bronchoscope 16 (which may be referred to as an unlocked state of the bronchoscope adapter 16*a*) or inhibit motion of the sEWC 14 relative to the bronchoscope 16 (which may be referred to as a locked state of the bronchoscope adapter 16*a*). Bronchoscope adapters 16*a*** are currently marketed and sold by Medtronic PLC under the brand names EDGE® Bronchoscope Adapter or the ILLUMISITE® Bronchoscope Adapter, and are contemplated as being usable with the disclosure.

A locatable guide (LG) 18, including one or more EM sensors **18*a* may be inserted into the sEWC 14 and selectively locked into position relative to the sEWC 14 such that the sensor 18*a* extends a desired distance beyond a distal tip of the sEWC 14. As can be appreciated, the sensor 18*a* is disposed on or in the LG 18 a predetermined distance from a distal end of the LG 18. It is contemplated that the EM sensor 18*a* may be a five degree-of-freedom sensor or a six degree-of-freedom sensor. In embodiments, the LG 18 may be locked relative to the sEWC 14 such that the EM sensor 18*a* of the LG 18 extends a first, predetermined fixed distance beyond the distal tip of the sEWC 14 to enable the system 10 to determine a position of a distal portion of the LG 18 within the luminal network of the patient. It is envisioned that the LG 18 may be selectively locked relative to the sEWC 14 at any time, regardless of the position of the distal end of the LG 18 relative to the sEWC 14. It is contemplated that the LG 18 may be selectively locked to a handle 12*a* of the catheter guide assembly 12** using any suitable means, such as for example, a snap fit, a press fit, a friction fit, a cam, one or more detents, threadable engagement, or a chuck clamp.

As compared to an EWC, the sEWC 14 includes one or more EM sensors **14*a* disposed in or on the sEWC 14 at a predetermined distance from the distal end of the sEWC 14. As can be appreciated, the EM sensor 14*a* is separate from the EM sensor 18*a* of the LG 18. It is contemplated that the EM sensor 14*a* may be a five degree-of-freedom sensor or a six degree-of-freedom sensor. It is envisioned that the sEWC 14 may be utilized in a manner similar to the LG 18, in which case the LG 18 may not be used. It is contemplated that the sEWC 14 and the LG 18 may be utilized together, in which data from the EM sensors 14*a* and 18*a* may be fused together. As can be appreciated, the position and orientation of the EM sensors 14*a* of the sEWC and 18*a* of the LG 18 relative to a reference coordinate system, and thus a distal portion of the sEWC 14 or LG 18, within an electromagnetic field can be derived. Catheter guide assemblies 12** are currently marketed and sold by Medtronic PLC under the brand names SUPERDIMENSION® Procedure Kits, ILLUMISITE™ Endobronchial Procedure Kit, ILLUMISITE™ Navigation Catheters, or EDGE® Procedure Kits, and are contemplated as being usable with the disclosure.

The system 10 includes a catheter 70 configured to be inserted into, and extend from the sEWC 14. The catheter 70 defines a distal end 72 having at least one camera 74 disposed thereon that is configured to capture real-time images or video. Although generally described as being disposed on the distal end 72 of the catheter 70, it is envisioned that the camera 74 may be disposed on any suitable location on the catheter 70, such as for example, a sidewall. In embodiments, the catheter 70 may include one or more light sources (not shown) disposed on or adjacent to the distal end 72 or any other suitable location (e.g., for example, a side surface or a protuberance). The light source may be or may include, for example, a light emitting diode (LED), an optical fiber connected to a light source that is located external to the patient, or combinations thereof, and may emit one or more of white, IR, or near infrared (NIR) light. In this manner, the camera 74 may be, for example, a white light camera, IR camera, or NIR camera, a camera that is capable of capturing white light and NIR light, or combinations thereof. In one non-limiting embodiment, the camera 74 is a white light mini complementary metal-oxide, semiconductor (CMOS) camera, although it is contemplated that the camera 74 may be any suitable camera, such as for example, a charge-coupled device (CCD), a complementary metal-oxide-semiconductor (CMOS), a N-type metal-oxide-semiconductor (NMOS), and in embodiments, may be an infrared (IR) camera, depending upon the design needs of the system 10. As can be appreciated, the camera 74 captures images of the patient's anatomy from a perspective of looking out from the distal end 72 of the catheter 70. It is envisioned that the catheter 70 may include one or more EM sensors 76 disposed adjacent to, or on, the distal end 72 of the catheter 70. It is contemplated that the EM sensor 76 may be a five degree-of-freedom sensor or a six degree-of-freedom sensor. As will be described in further detail hereinbelow, the position and orientation of the EM sensor 76 of the catheter 70 relative to a reference coordinate system, and thus a distal portion of the catheter 70, within an electromagnetic field can be derived.

With continued reference to FIG. 1, the system 10 generally includes an operating table 52 configured to support a patient P and monitoring equipment 24 coupled to the sEWC 14, the bronchoscope 16, or the endoscope 70 (e.g., for example, a video display for displaying the video images received from the video imaging system of the bronchoscope 12 or the camera 74 of the catheter 70), a locating or tracking system 46 including a tracking module 48, a plurality of reference sensors 50 and a transmitter mat 54 including a plurality of incorporated markers, and a workstation 20 having a computing device 22 including software and/or hardware used to facilitate identification of a target, pathway planning to the target, navigation of a medical device to the target, and/or confirmation and or determination of placement of, for example, the sEWC 14, the bronchoscope 16, the LG 18, the catheter 70, or a surgical tool, relative to the target.

The tracking system 46 is, for example, a six degrees-of-freedom electromagnetic locating or tracking system, or other suitable system for determining position and orientation of, for example, a distal portion the sEWC 14, the bronchoscope 16, the LG 18, the catheter 70, or a surgical tool, for performing registration of a detected position of one or more of the EM sensors 14*a*, 18*a*, or 76 and a three-dimensional (3D) model generated from a CT, CBCT, or MRI image scan. The tracking system 46 is configured for use with the sEWC 14, the LG 18, and the catheter 70, and particularly with the EM sensors 14*a*, 18*a*, and 74.

Continuing with FIG. 1, the transmitter mat 54 is positioned beneath the patient P. The transmitter mat 54 generates an electromagnetic field around at least a portion of the patient P within which the position of the plurality of reference sensors 50 and the EM sensors 14*a*, 18*a*, and 74 can be determined with the use of the tracking module 48. In one non-limiting embodiment, the transmitter mat 54 generates three or more electromagnetic fields. One or more of the reference sensors 50 are attached to the chest of the patient P. Registration is generally performed using coordinate locations of the 3D model and 2D images from the planning phase, with the patient P's airways as observed through the bronchoscope 12 or catheter 70 and allow for the navigation phase to be undertaken with knowledge of the location of the EM sensors 14*a*, 18*a*, and 74. It is envisioned that any one of the EM sensors 14*a*, 18*a*, and 70 may be a single coil sensor that enables the system 10 to identify the position of the sEWC 14, the LG 18, or the catheter 70 within the EM field generated by the transmitter mat 54, although it is contemplated that the EM sensors 14*a*, 18*a*, and 70 may be any suitable sensor and may be a sensor capable of enabling the system 10 to identify the position, orientation, and/or pose of the sEWC 14, the LG, or the catheter within the EM field.

Registration of the patient P's location on the transmitter mat 54 may be performed by moving the EM sensors 14*a*, 18*a*, or 74 through the airways of the patient P. In this manner, data pertaining to the locations of the EM sensors 14*a*, 18*a*, or 74, while the sEWC 14, the LG 18*a*, or the catheter 70 is moving through the airways, is recorded using the transmitter mat 54, the reference sensors 50, and the tracking system 46. A shape resulting from this location data is compared to an interior geometry of passages of a 3D model, and a location correlation between the shape and the 3D model based on the comparison is determined, e.g., for example, utilizing the software on the computing device 22. In addition, the software identifies non-tissue space (e.g., for example, air filled cavities) in the 3D model. The software aligns, or registers, an image representing a location of the EM sensors 14*a*, 18*a*, or 70 with the 3D model and/or 2D images generated from the 3D model, which are based on the recorded location data and an assumption that the sEWC 14, the LG 18, or the catheter 70 remains located in non-tissue space in a patient's airways. In embodiments, a manual registration technique may be employed by navigating the sEWC 14, LG 18, or catheter 70 with the EM sensors 14*a*, 18*a*, or 74 to pre-specified locations in the lungs of the patient P, and manually correlating the images from the bronchoscope 16 or the catheter 70 to the model data of the 3D model.

Although generally described with respect to EMN systems using EM sensors, the instant disclosure is not so limited and may be used in conjunction with flexible sensors, such as for example, fiber-bragg grating sensors, inertial measurement units (IMU), ultrasonic sensors, without sensors, or combinations thereof. It is contemplated that the devices and systems described herein may be used in conjunction with robotic systems such that robotic actuators drive the sEWC 14 or bronchoscope 16 proximate the target.

In accordance with aspects of the disclosure, the visualization of intra-body navigation of a medical device (e.g., for example a biopsy tool or a therapy tool), towards a target (e.g., for example, a lesion) may be a portion of a larger workflow of a navigation system. An imaging device 56 (e.g., for example, a CT imaging device, such as for example, a cone-beam computed tomography (CBCT) device, including but not limited to Medtronic plc's O-Arm™ system) capable of acquiring 2D and 3D images or video of the patient P is also included in the particular aspect of system 10. The images, sequence of images, or video captured by the imaging device 56 may be stored within the imaging device 56 or transmitted to the computing device 22 for storage, processing, and display. In embodiments, the imaging device 56 may move relative to the patient P so that images may be acquired from different angles or perspectives relative to the patient P to create a sequence of images, such as for example, a fluoroscopic video. The pose of the imaging device 56 relative to the patient P while capturing the images may be estimated via markers incorporated with the transmitter mat 54. The markers are positioned under the patient P, between the patient P and the operating table 52, and between the patient P and a radiation source or a sensing unit of the imaging device 56. The markers incorporated with the transmitter mat 54 may be two separate elements which may be coupled in a fixed manner or alternatively may be manufactured as a single unit. It is contemplated that the imaging device 56 may include a single imaging device or more than one imaging device.

Figure 2:
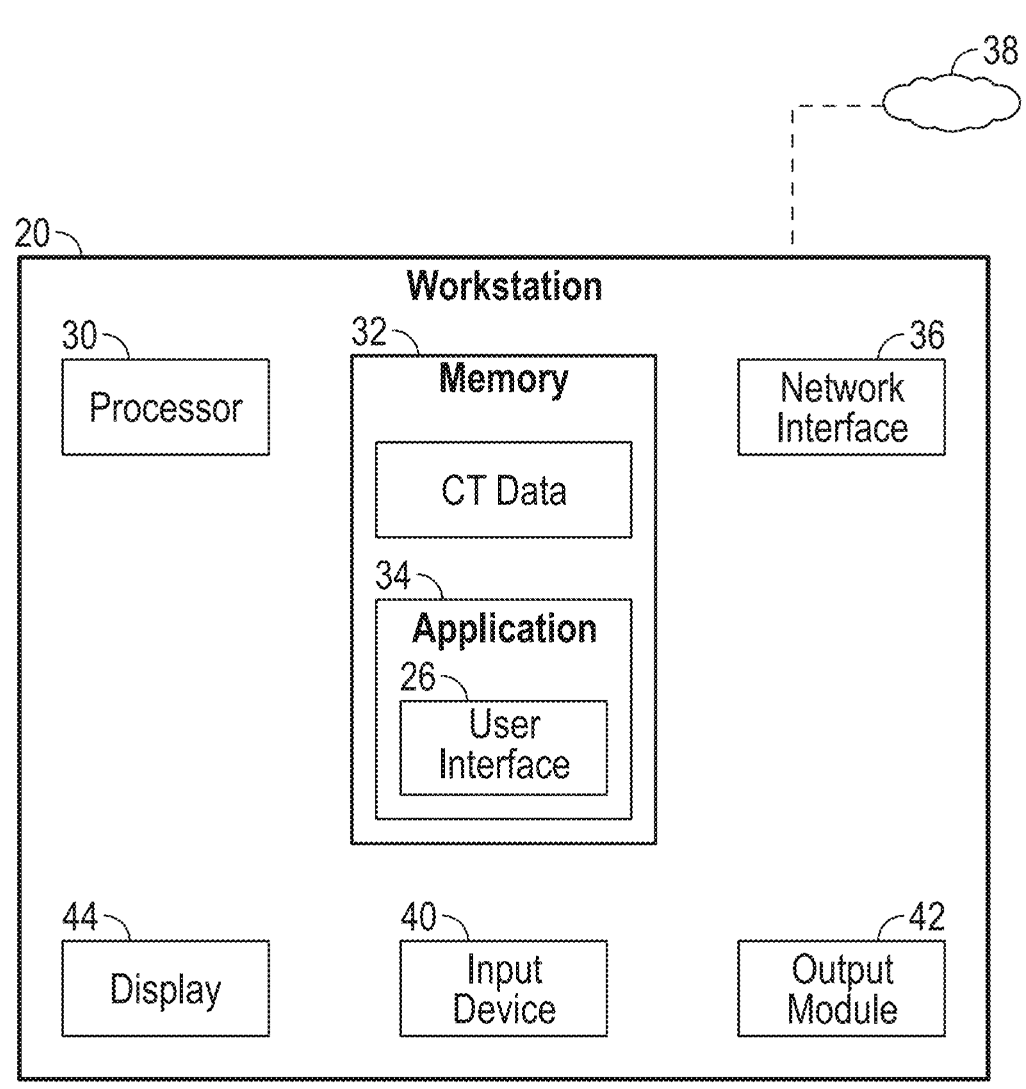
FIG. 2 is a schematic view of a workstation of the surgical system of FIG. 1.

Continuing with FIG. 1 and with additional reference to FIG. 2, the workstation 20 includes a computer 22 and a display 24 that is configured to display one or more user interfaces 26 and/or 28. The workstation 20 may be a desktop computer or a tower configuration with the display 24 or may be a laptop computer or other computing device. The workstation 20 includes a processor 30 which executes software stored in a memory 32. The memory 32 may store video or other imaging data captured by the bronchoscope 16 or catheter 70 or pre-procedure images from, for example, a computer-tomography (CT) scan, Positron Emission Tomography (PET), Magnetic Resonance Imaging (MRI), or Cone-beam CT (CBCT). In addition, the memory 32 may store one or more applications 34 to be executed on the processor 30. Though not explicitly illustrated, the display 24 may be incorporated into a head mounted display such as for example, an augmented reality (AR) headset such as the HoloLens offered by Microsoft Corp.

A network interface 36 enables the workstation 20 to communicate with a variety of other devices and systems via the Internet. The network interface 36 may connect the workstation 20 to the Internet via a wired or wireless connection. Additionally, or alternatively, the communication may be via an ad-hoc Bluetooth® or wireless network enabling communication with a wide-area network (WAN) and/or a local area network (LAN). The network interface 36 may connect to the Internet via one or more gateways, routers, and network address translation (NAT) devices. The network interface 36 may communicate with a cloud storage system 38, in which further image data and videos may be stored. The cloud storage system 38 may be remote from or on the premises of the hospital such as for example, in a control or hospital information technology room. An input module 40 receives inputs from an input device such as for example, a keyboard, a mouse, or voice commands. An output module 42 connects the processor 30 and the memory 32 to a variety of output devices such as for example, the display 24. In embodiments, the workstation 20 may include its own display 44, which may be a touchscreen display.

With continued reference to FIG. 2, one of the applications 34 stored in the memory 32 and executed by the processor 30 may determine the position of the EM sensors 14*a*, 18*a*, or 70 in the EM field generated by the transmitter mat 54. The determination of the position of the sEWC 14, the LG 18, or the catheter 70 and the camera 74 of the catheter 70 enables one method in which the images captured by the camera 74 of the catheter 70 may be registered to a generated 3D model of the patient's anatomy, as will be described in further detail hereinbelow.

In a planning or pre-procedure phase, the software stored in the memory 32 and executed by the processor 30 utilizes pre-procedure CT image data, either stored in the memory 32 or retrieved via the network interface 36, for generating and viewing a 3D model of the patient's anatomy, enabling the identification of target tissue on the 3D model (automatically, semi-automatically, or manually), and in embodiments, allowing for the selection of a pathway through the patient's anatomy to the target tissue. One example of such an application is the ILOGIC® planning and navigation suites currently marketed by Medtronic. The 3D model may be displayed on the display 24 or another suitable display associated with the workstation 20, such as for example, the display 44, or in any other suitable fashion. Using the workstation 20, various views of the 3D model may be provided and/or the 3D model may be manipulated to facilitate identification of target tissue on the 3D model and/or selection of a suitable pathway to the target tissue.

In embodiments, the software stored in the memory 32 may identify and segment out a targeted critical structure within the 3D model. It is envisioned that the segmentation process may be performed automatically, manually, or a combination of both. The segmentation process isolates the targeted critical structure from the surrounding tissue in the 3D model and identifies its position within the 3D model. As can be appreciated, this position can be updated depending upon the view selected on the display 24 such that the view of the segmented targeted critical structure may approximate a view captured by the catheter 70, as will be described in further detail hereinbelow.

Figures 3, 4, 5:
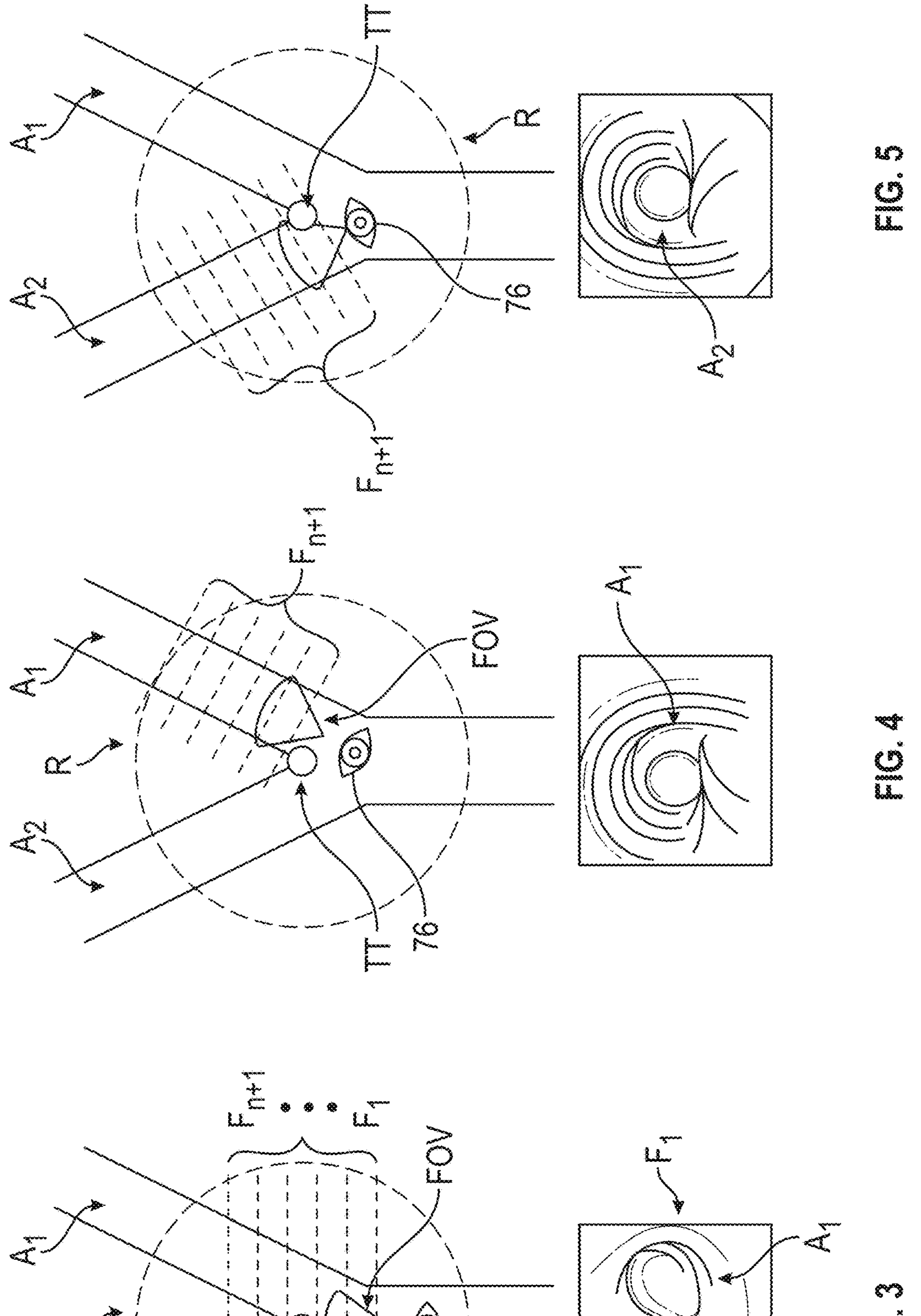
FIG. 3 is a schematic view of a camera of a catheter of the surgical system of FIG. 1 capturing images from a first direction in accordance with the disclosure.
FIG. 4 is a schematic view of the camera of the catheter of FIG. 3 capturing images from a second direction in accordance with the disclosure.
FIG. 5 is a schematic view of the camera of the catheter of FIG. 3 capturing images from a third direction in accordance with the disclosure.

With reference to FIGS. 3-5, during a navigation phase, the sEWC 14 is navigated through the luminal network of the patient to a position adjacent to the target tissue TT according to the selected pathway to the target tissue TT. It is contemplated that the sEWC 14 may be navigated to the position adjacent to the target tissue TT using the LG 18 or the catheter 70, or may be navigated to the position adjacent to the target tissue TT using only the EM sensor 14*a* of the sEWC 14 (neither the LG 18 nor the catheter 70 being advanced within the sEWC). In one non-limiting embodiment, the sEWC 14 is navigated to the position adjacent to the target tissue TT using the catheter 70. In this manner, the software stored in the memory 32 communicates with the EM sensor 76 and the camera 74 of the catheter 70 to determine a position of the catheter 70 within the patient's airways and capture images in real-time of the patient's anatomy as the catheter 70 is navigated through the luminal network of the patient. Using the camera 74 of the catheter 70, the distal end 72 of the catheter 70 is manipulated to a position where the target tissue TT is within a field of view (FOV) of the camera 74 (e.g., for example, the target tissue TT is entirely encompassed within the field of view of the camera 74). As can be appreciated, the position of the distal end 72 of the catheter 70 relative to the target tissue TT may be determined using the real-time images captured by the camera 74 and displayed on one or both of the user interfaces 26, 28. With the catheter 70 positioned at the desired location relative to the target tissue TT, a first frame or image $F_1$, which may be a still image, is captured and the coordinates of the location of the catheter 70 within the patient's anatomy as the first frame $F_1$ is captured are determined using the EM sensor 76. As can be appreciated, movement of the catheter 70 while capturing the first frame $F_1$ can cause inaccuracies when determining the coordinates of the catheter 70, and therefore, movement of the catheter 70 while capturing the first frame $F_1$ should be minimized. The determined coordinates of the catheter 70 as the first frame $F_1$ is captured are associated or otherwise assigned to the first image $F_1$. It is contemplated that the coordinates of the catheter 70 may include one or more of an x-position, a y-position, a z-position, pitch, yaw, and roll. In this manner, the first frame $F_1$ may be assigned coordinates $x_1$, $y_1$, $z_1$, $P_1$, $Y_1$, $R_1$, wherein $x_1$ is the x-position of the catheter 70 when the first frame $F_1$ was captured, $y_1$ is the y-position of the catheter 70 when the first frame $F_1$ was captured, $z_1$ is the z-position of the catheter 70 when the first frame $F_1$ was captured, $P_1$ is the pitch angle of the catheter 70 when the first frame $F_1$ was captured, $Y_1$ is the yaw angle of the catheter 70 when the first frame $F_1$ was captured, and $R_1$ is the roll angle of the catheter 70 when the first frame $F_1$ was captured.

With the first frame $F_1$ captured by the camera 74 of the catheter 70, the software application determines a radius R extending from a center of the target tissue TT within which further images or frames $F_{n+1}$ are to be captured by the camera 74 of the catheter 70. It is envisioned that the radius R may extend any distance from the target tissue TT depending upon anatomy of the patient surrounding the target tissue TT (e.g., for example, a number of bifurcations surrounding the target tissue TT or a length of the airway adjacent to the target tissue TT). The catheter 70 is advanced a desired distance, which may be a predetermined distance, towards the target tissue TT, at which time a second image or frame is captured by the camera 74 of the endoscope 70 and the coordinates of the catheter 70 within the patient's anatomy as the second frame is captured is determined and assigned or otherwise associated with the second frame. Thereafter, the catheter 70 is advanced a desired distance, which may be the predetermined distance, at which time a third image or frame is obtained by the camera 74 of the catheter 70 and the coordinates of the catheter 70 within the patient's anatomy as the third frame is captured is determined and assigned or otherwise associated with the third frame. Each successive frame $F_{n+1}$ is obtained in a substantially similar manner as described hereinabove until the position of the catheter 70 is either unable to be further advanced within the airway of the patient due to the presence of a tissue wall (e.g., for example, a bifurcation), the target tissue TT itself (e.g., for example, the camera 74 abuts or otherwise contacts the target tissue TT), or the extents of the radius R have been reached. If the radius R extends past a bifurcation, the catheter 70 is first advanced within a first airway or lumen $A_1$ (FIG. 4) and additional images or frames $F_{n+1}$ are obtained at successive locations until the catheter 70 is unable to be further advanced or the extents of the radius R have been reached. Thereafter, the catheter 70 is advanced within the second airway or lumen $A_2$ (FIG. 5) and additional images or frames $F_{n+1}$ are obtained at successive locations until the catheter 70 is unable to be further advanced or the extents of the radius R have been reached. As can be appreciated, the above process may be repeated as many times as necessary depending upon the number of airways or lumens branching off of the bifurcation or the number of additional bifurcations and lumens or airways located within the extents of the radius R.

Although generally described as obtaining each frame $F_{n+1}$ while the catheter 70 is stationary, it is envisioned that the camera 74 of the catheter may obtain real-time video as the catheter 70 is advanced within the airways of the patient P within the extents of the radius R. As can be appreciated, the location of the EM sensor 76 of the catheter 70 is tracked by the tracking system 46 in real-time, and therefore, the position or coordinates of the catheter 70 within the patient P's airways can be determined and assigned to each frame $F_{n+1}$ of the real-time video.

With the necessary frames $F_{n+1}$ obtained and the corresponding coordinates of the catheter 70 determined or assigned, the software application generates a 3D model of the patient P's airways using each frame $F_{n+1}$ and their associated coordinates. In one non-limiting embodiment, the software application generates the 3D model using a simultaneous localization and mapping (SLAM) algorithm, although it is contemplated that any suitable algorithm may be utilized to generate the 3D model without departing from the scope of the present disclosure.

Figure 6:
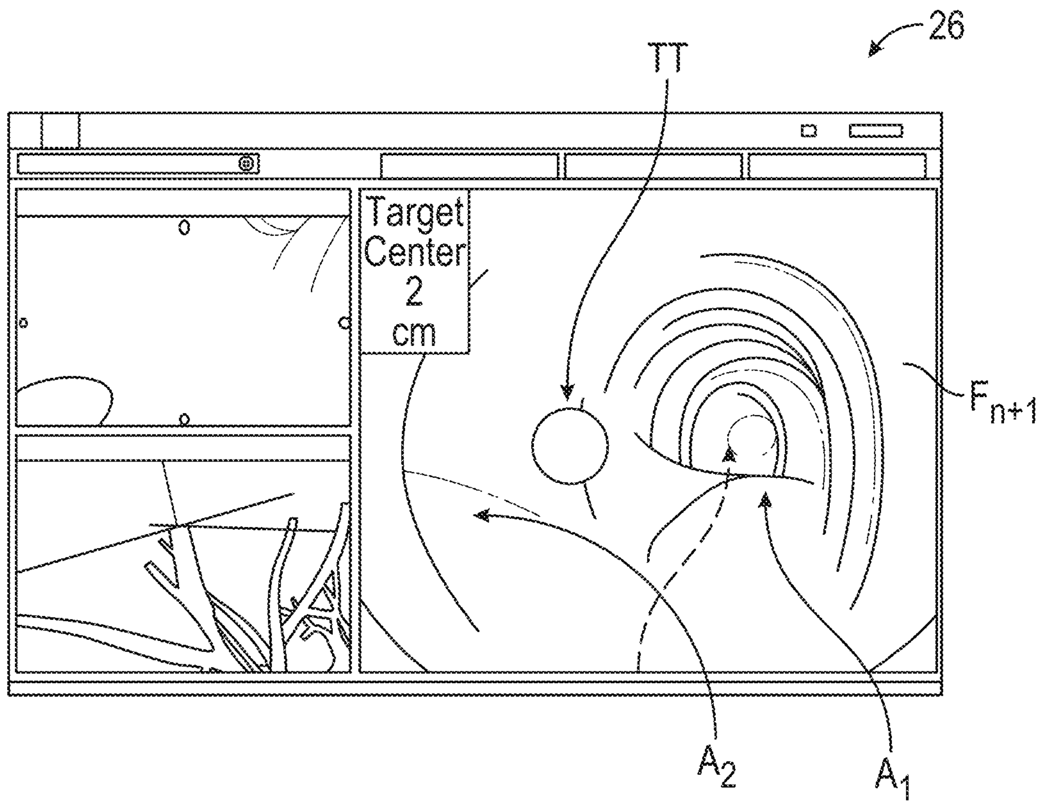
FIG. 6 is a depiction of a graphical user interface of the surgical system of FIG. 1 illustrating an image captured by the camera of the catheter of FIG. 3 corresponding to a location of a biopsy tool of the surgical system of FIG. 1.
Figure 7:
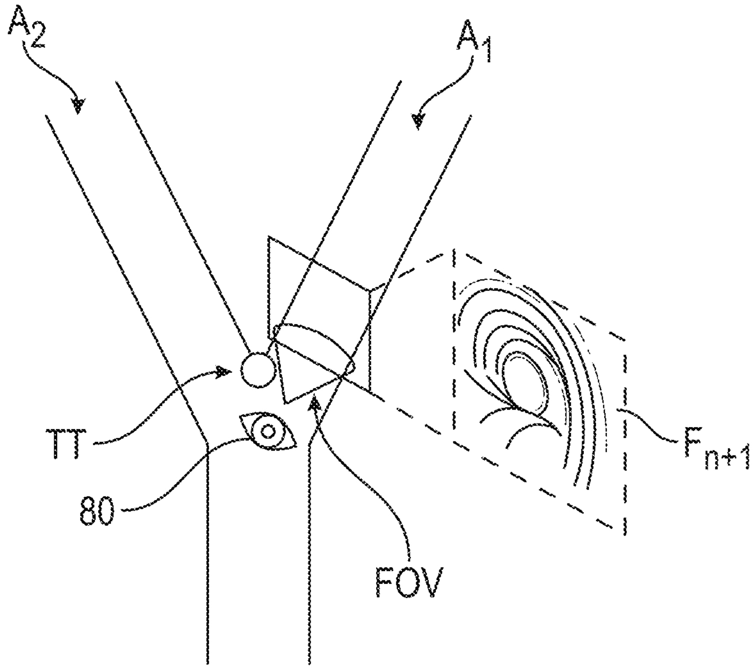
FIG. 7 is a schematic view illustrating identification of an image captured by the camera of the catheter of FIG. 3 corresponding to a location of the biopsy tool.
Figure 8:
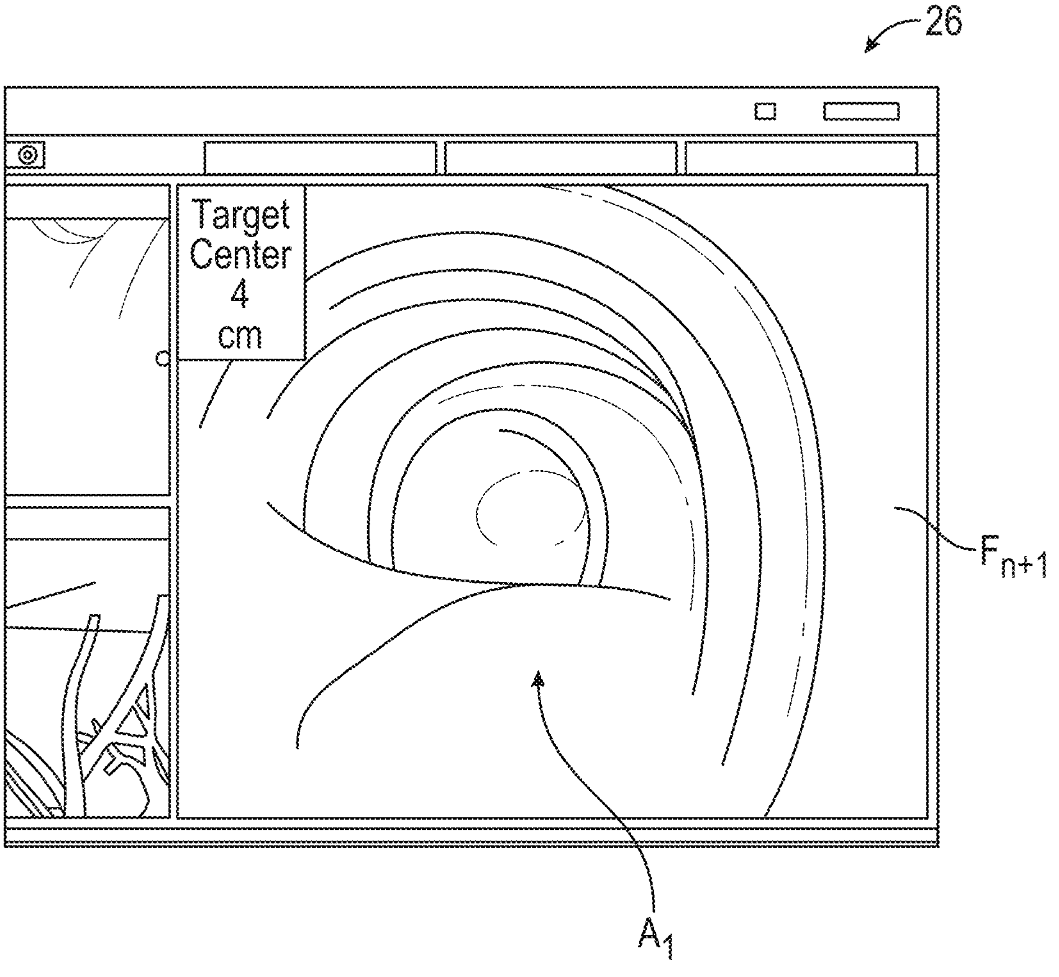
FIG. 8 is a depiction of the graphical user interface of the surgical system of FIG. 1 illustrating the identified image captured by the camera displayed on the graphical user interface.

With reference to FIGS. 6-8, after obtaining each frame $F_{n+1}$ and the corresponding coordinates of the catheter 70 determined, the catheter 70 is removed from the sEWC 14 and a tool or other medical device, such as for example, a biopsy device 80 (FIG. 1) is advanced within the working channel of the sEWC 14 and extended past the distal end of the sEWC 14. The biopsy device 80 may include an EM sensor 82 disposed on or within a distal end 84 of the biopsy device 80, or in embodiments, adjacent to the distal end 84. The EM sensor 82 of the biopsy device 80 is configured to be tracked by the tracking system 46 in a manner substantially similar to that of the EM sensors **14*a*, 18*a*, and 74 of the sEWC 14, LG 18, and catheter 70. In this manner, the software application communicates with the tracking system 46 to determine the position or coordinates of the biopsy device 80** within the airways of the patient P.

Turning to FIGS. 6-8, as can be appreciated, with the catheter 70 removed from the sEWC 14, visual observation of the patient P's anatomy adjacent to the target tissue TT is no longer available. Additionally, removal of the catheter 70 from the sEWC 14, or external forces acting upon the sEWC 14 (e.g., for example, tidal breathing) may cause the position of the sEWC 14 relative to the target tissue TT may shift resulting in inaccurate placement of the biopsy tool 80 relative to the target tissue TT. In accordance with the disclosure, the software stored in the memory 32 communicates with the EM sensor 82 of the biopsy device to determine the position and coordinates of the distal end 84 of the biopsy device 80 within the airways of the patient P. In this manner, the software stored on the memory 32 determines or identifies which frame $F_{n+1}$ correlates to the position and coordinates of the biopsy device 80 and displays the identified frame $F_{n+1}$ on one or both of the user interfaces 26, 28 to enable viewing of the patient P's anatomy adjacent the target tissue TT. As can be appreciated, the software stored on the memory 32 monitors the position and orientation of the biopsy device 80 in real-time and updates the displayed frame $F_{n+1}$ as necessary in real-time. In embodiments, the software stored on the memory 32 may display the 3D model on one or both of the user interfaces 26, 28 as would be viewed from the camera 74 of the catheter 70. It is contemplated that the software stored on the memory 32 may display a fly-through view (e.g., for example, a video or 3D space) on one or both of the user interfaces 26, 28 as the biopsy device 80 is manipulated adjacent to the target tissue TT. As can be appreciated, displaying the appropriate frame Fn+1, 3D model of the patient P's anatomy adjacent the target tissue TT generated from the images or frames Fn+1 captured by the camera 74 of the catheter 70 within the radius R, or fly-through view enables visualization of the patient P's anatomy adjacent the target tissue TT while manipulating the biopsy tool 80 and enables accurate placement of the biopsy tool 80 relative to the target tissue TT when obtaining a biopsy sample.

Figure 9A:
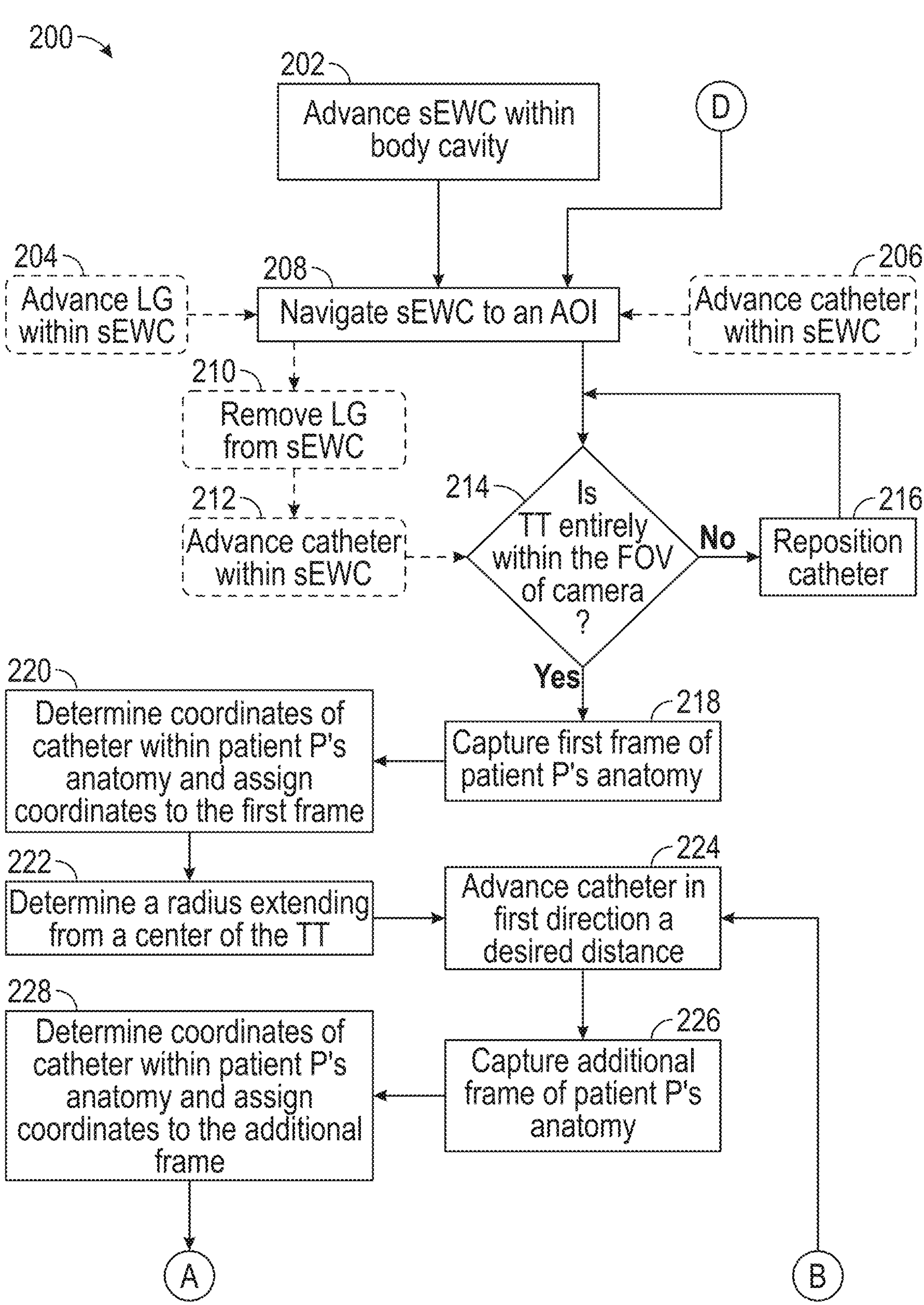
FIG. 9A is a flow diagram of a method of performing a surgical procedure using the surgical system of FIG. 1 in accordance with the disclosure.
Figure 9B:
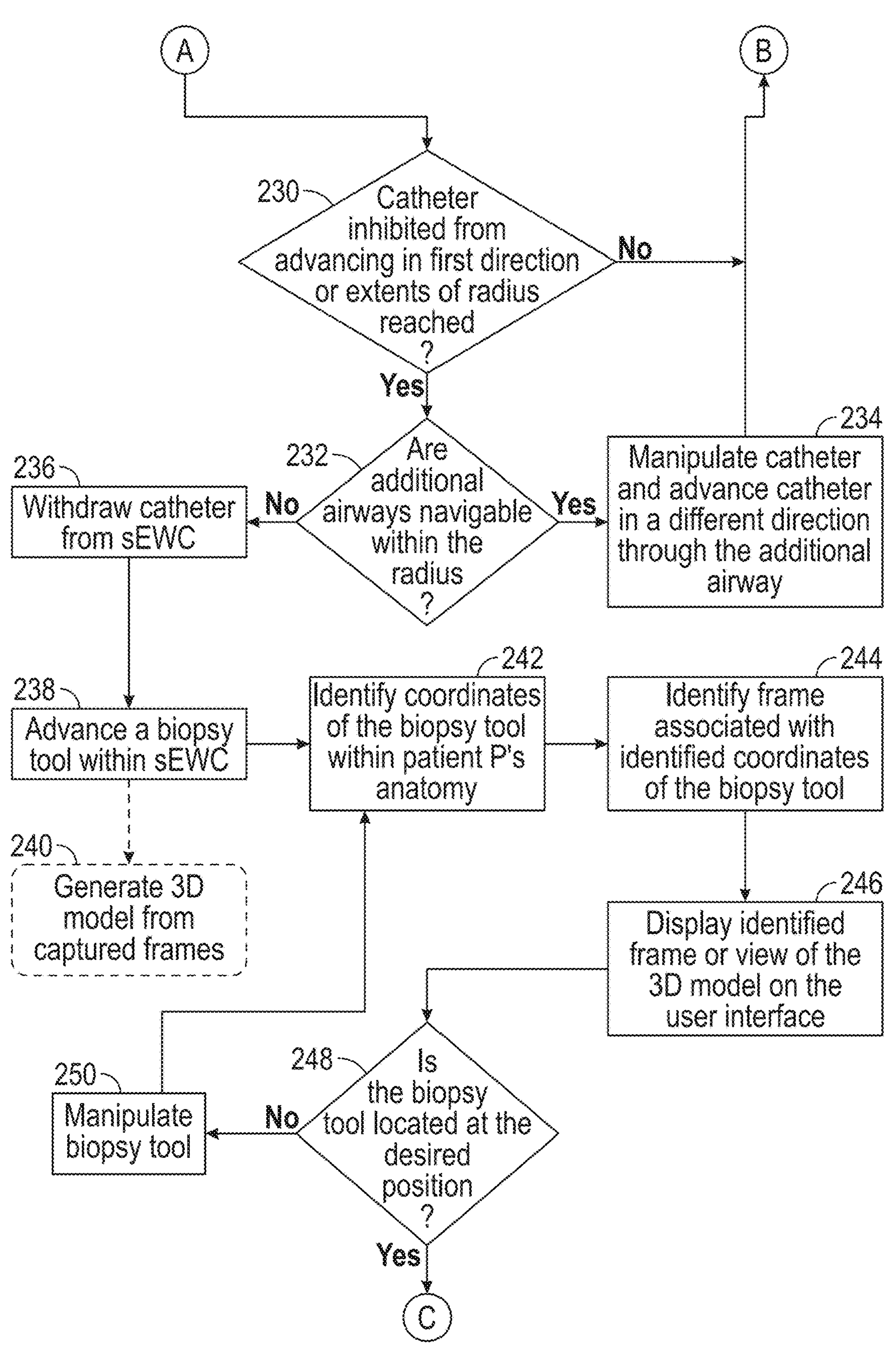
FIG. 9B is a continuation of the flow diagram of FIG. 9A.
Figure 9C:
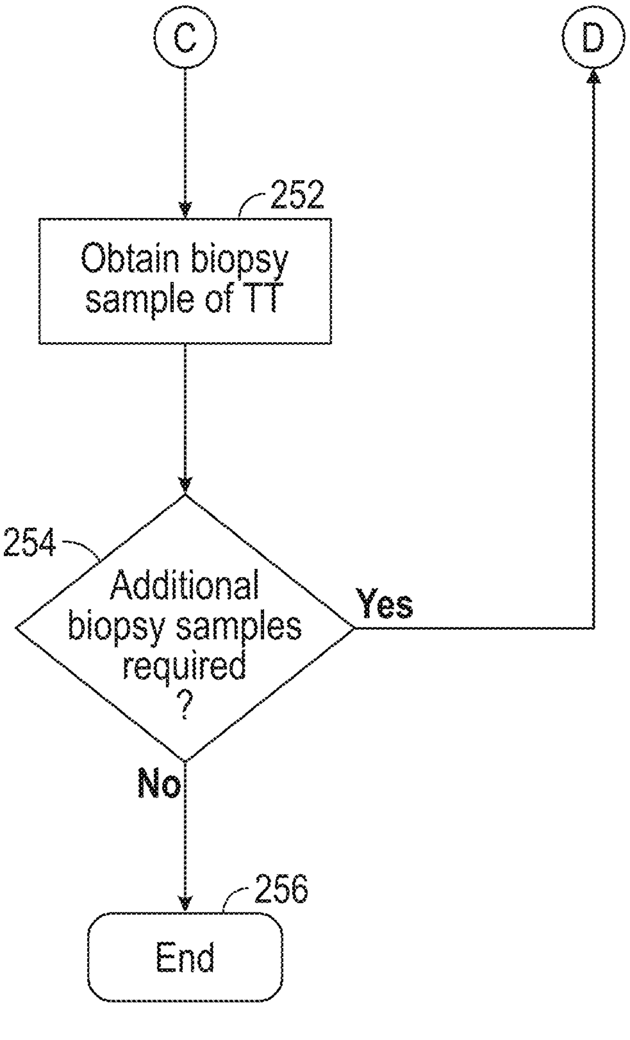
FIG. 9C is a continuation of the flow diagrams of FIGS. 9A and 9B.

With reference to FIGS. 9A-9C, a method of performing a surgical procedure is illustrated and generally identified by reference numeral 200. Initially, at step 202, the sEWC 14 is advanced within a body cavity of a patient P. If the LG 18 is used to navigate the sEWC 14 to the area of interest (AOI), the LG 18 is advanced within the sEWC 14 in step 204. If the catheter 70 is used to navigate the sEWC 14 to the area of interest (AOI), the catheter 70 is advanced within the sEWC 14 in step 206. In step 208, the sEWC 14 is navigated to the area of interest. With the distal end of the sEWC 14 located adjacent target tissue TT within the area of interest (AOI), in step 210, the LG 18 is removed from the sEWC and the catheter 70 is advanced within extended beyond the distal end of the sEWC 14 in step 212. In step 214, it is determined if the distal end 72 of the catheter 70 disposed at a position where the target tissue TT is entirely within the field of view FOV of the camera 76. If the target tissue TT is not entirely within the field of view FOV of the camera 76, the catheter 70 is repositioned until the target tissue TT is entirely within the field of view of the FOV in step 216. If the target tissue TT is entirely within the field of view FOV of the camera 76, in step 218, a first image or frame $F_1$ of the patient P's anatomy is captured and in step 220, the position and/or coordinates of the catheter 70 within the patient P's anatomy when the first frame $F_1$ was captured is determined and assigned or associated with the first frame $F_1$. In step 222, a radius R extending from a center of the target tissue TT is determined, within which further images or frames $F_{n+1}$ are to be captured by the camera 74 of the catheter 70. With the radius R determined, in step 224, the catheter 70 is advanced within the body cavity of the patient P in a first direction a desired distance and a second image or frame $F_{n+1}$ is captured by the camera 76 in step 226. In step 228, the position and/or coordinates of the catheter 70 within the patient P's anatomy when the second frame $F_{n+1}$ was captured is determined and assigned or associated with the second frame $F_{n+1}$. In step 230, it is determined if the catheter 70 is inhibited from further advancement in the first direction within the body cavity of the patient P (e.g., for example, the catheter abuts or otherwise contacts a tissue wall or bifurcation) or the catheter 70 has reached the extents of the radius R. If the catheter 70 is able to be further advanced in the first direction and has not reached the extents of the radius R, the method returns to step 224 and further images or frames $F_{n+1}$ are obtained. If the catheter is unable to be further advanced or has reached the extents of the radius R while being advanced in the first direction, in step 232, it is determined if additional lumens or airways $A_1$ or $A_2$ are navigable within the extents of the radius R. If it is determined that further airways $A_1$ or $A_2$ are navigable within the extents of the radius R, in step 234, the catheter 70 is manipulated to advance through one of the airways $A_1$ or $A_2$, and the method returns to step 224. If it is determined that no further airways $A_1$ or $A_2$ are navigable within the extents of the radius R, in step 236, the catheter 70 is withdrawn from the sEWC and in step 238, a biopsy tool 80 is advanced within and extended past the distal end 72 of the sEWC 14. Optionally, in step 240, a 3D model of the patient P's anatomy adjacent to the target tissue TT is generated from the captured frames $F_{n+1}$. In step 242, a position and/or coordinates of the biopsy tool 80 within the patient P's anatomy is determined, and in step 244, a frame $F_{n+1}$ associated with the determined position and/or coordinates of the biopsy tool 80 is identified. In step 246, the identified frame $F_{n+1}$ or view of the 3D model is displayed on one or both of the user interface's 26, 28. In step 248, it is determined if the biopsy tool 80 is located at a desired location relative to the target tissue TT. If the biopsy tool 80 is not located at the desired location, in step 250 the biopsy tool 80 is manipulated relative to the target tissue TT and the method returns to step 242 until the biopsy tool 80 is positioned at the desired location relative to the target tissue TT. If the biopsy tool 80 is located at the desired location, a biopsy of the target tissue TT is obtained in step 252. In step 254, it is determined if additional biopsy samples are required. If additional biopsy samples are required, the method returns to step 208 until no further biopsy samples are required. If no further biopsy samples are required, the ends at step 256. As can be appreciated, the method described herein above may be performed as many times as necessary without departing from the scope of the present disclosure.

Figure 10:
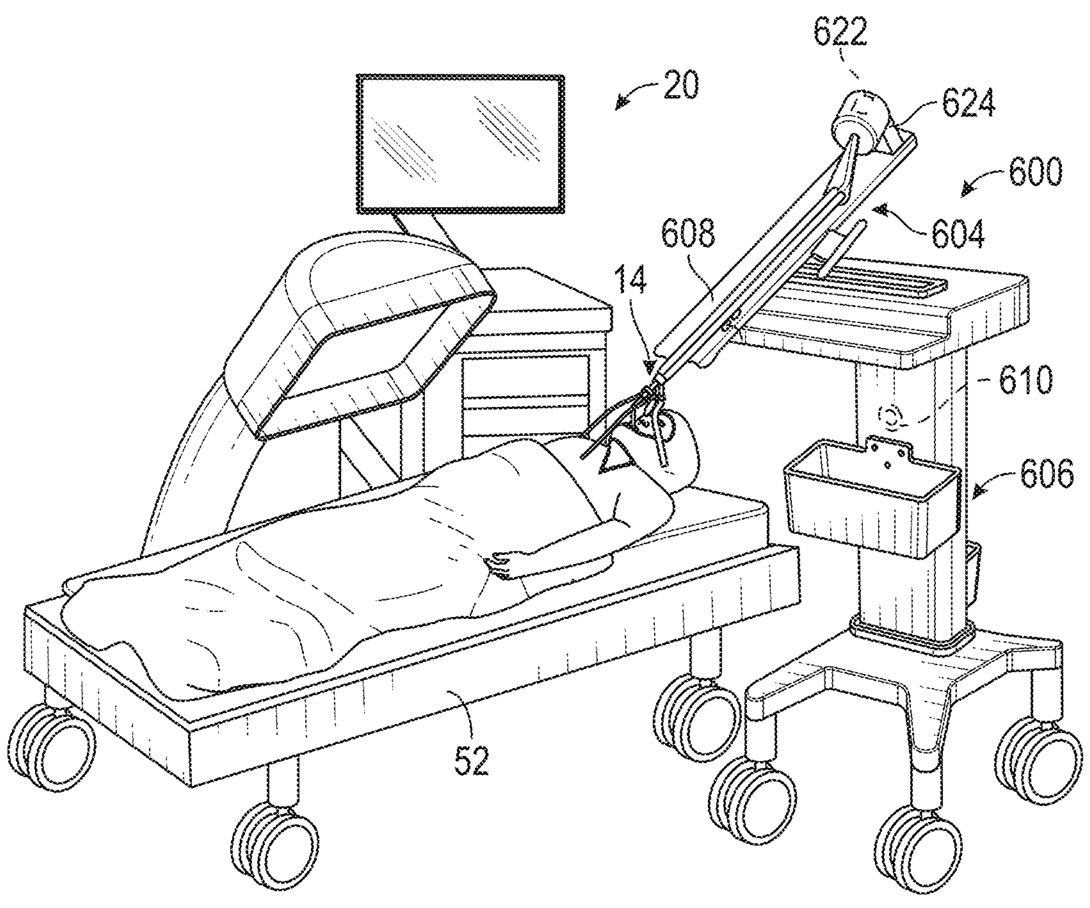
FIG. 10 is a perspective view of a robotic surgical system of the surgical system of FIG. 1.
Figure 11:
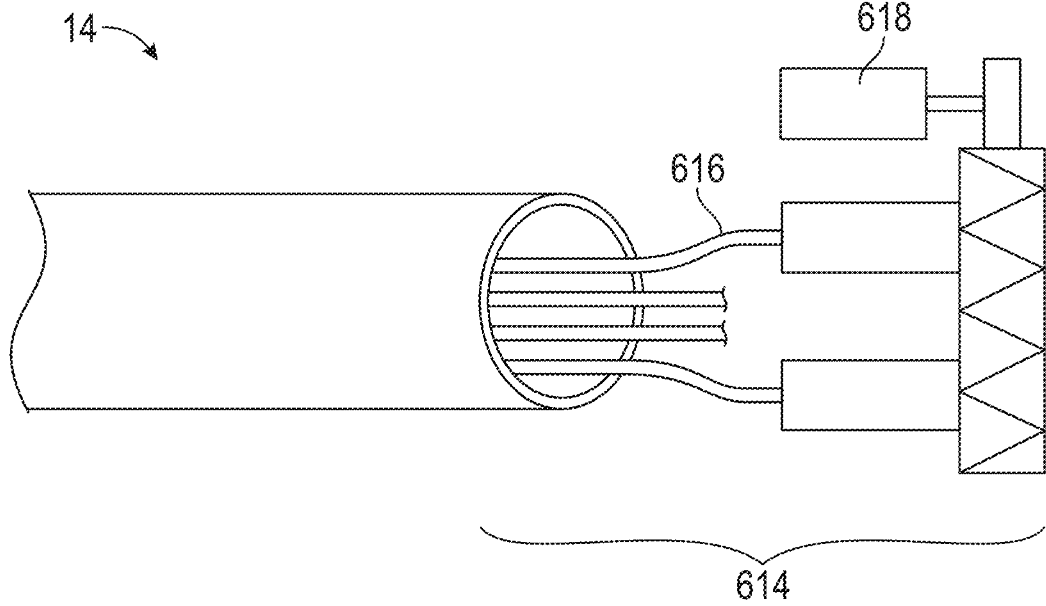
FIG. 11 is an exploded view of a drive mechanism of an extended working channel of the surgical system of FIG. 1.

With reference to FIGS. 10 and 11, it is envisioned that the system 10 may include a robotic surgical system 600 having a drive mechanism 602 including a robotic arm 604 operably coupled to a base or cart 606, which may, in embodiments, be the workstation 20. The robotic arm 604 includes a cradle 608 that is configured to receive a portion of the sEWC 14. The sEWC 14 is coupled to the cradle 608 using any suitable means (e.g., for example, straps, mechanical fasteners, and/or couplings). It is envisioned that the robotic surgical system 600 may communicate with the sEWC 14 via electrical connection (e.g., for example, contacts and/or plugs) or may be in wireless communication with the sEWC 14 to control or otherwise effectuate movement of one or more motors (FIG. 11) disposed within the sEWC 14 and receive images captured by a camera (not shown) associated with the sEWC 14. In this manner, it is contemplated that the robotic surgical system 600 may include a wireless communication system 610 operably coupled thereto such that the sEWC 14 may wirelessly communicate with the robotic surgical system 600 and/or the workstation 20 via Wi-Fi, Bluetooth®, for example. As can be appreciated, the robotic surgical system 600 may omit the electrical contacts altogether and may communicate with the sEWC 14 wirelessly or may utilize both electrical contacts and wireless communication. The wireless communication system 610 is substantially similar to the network interface 36 (FIG. 2) described hereinabove, and therefore, will not be described in detail herein in the interest of brevity. As indicated hereinabove, the robotic surgical system 600 and the workstation 20 may be one in the same, or in embodiments, may be widely distributed over multiple locations within the operating room. It is contemplated that the workstation 20 may be disposed in a separate location and the display 44 (FIGS. 1 and 2) may be an overhead monitor disposed within the operating room.

As indicated hereinabove, it is envisioned that the sEWC 14 may be manually actuated via cables or push wires, or for example, may be electronically operated via one or more buttons, joysticks, toggles, actuators (not shown) operably coupled to a drive mechanism 614 disposed within an interior portion of the sEWC 14 that is operably coupled to a proximal portion of the sEWC 14, although it is envisioned that the drive mechanism 614 may be operably coupled to any portion of the sEWC 14. The drive mechanism 614 effectuates manipulation or articulation of the distal end of the sEWC 14 in four degrees of freedom or two planes of articulation (e.g., for example, left, right, up, or down), which is controlled by two push-pull wires, although it is contemplated that the drive mechanism 614 may include any suitable number of wires to effectuate movement or articulation of the distal end of the sEWC 14 in greater or fewer degrees of freedom without departing from the scope of the present disclosure. It is contemplated that the distal end of the sEWC 14 may be manipulated in more than two planes of articulation, such as for example, in polar coordinates, or may maintain an angle of the distal end relative to the longitudinal axis of the sEWC 14 while altering the azimuth of the distal end of the sEWC 14 or vice versa. In one non-limiting embodiment, the system 10 may define a vector or trajectory of the distal end of the sEWC 14 in relation to the two planes of articulation.

It is envisioned that the drive mechanism 614 may be cable actuated using artificial tendons or pull wires 616 (e.g., for example, metallic, non-metallic, and/or composite) or may be a nitinol wire mechanism. In embodiments, the drive mechanism 614 may include motors 618 or other suitable devices capable of effectuating movement of the pull wires 616. In this manner, the motors 618 are disposed within the sEWC 14 such that rotation of an output shaft the motors 618 effectuates a corresponding articulation of the distal end of the sEWC 14.

Although generally described as having the motors 618 disposed within the sEWC 14, it is contemplated that the sEWC 14 may not include motors 618 disposed therein. Rather, the drive mechanism 614 disposed within the sEWC 14 may interface with motors 622 disposed within the cradle 608 of the robotic surgical system 600. In embodiments, the sEWC 14 may include a motor or motors 618 for controlling articulation of the distal end 138 of the sEWC 14 in one plane (e.g., for example, left/null or right/null) and the drive mechanism 624 of the robotic surgical system 600 may include at least one motor 622 to effectuate the second axis of rotation and for axial motion. In this manner, the motor 618 of the sEWC 14 and the motors 622 of the robotic surgical system 600 cooperate to effectuate four-way articulation of the distal end of the sEWC 14 and effectuate rotation of the sEWC 14. As can be appreciated, by removing the motors 618 from the sEWC 14, the sEWC 14 becomes increasingly cheaper to manufacture and may be a disposable unit. In embodiments, the sEWC 14 may be integrated into the robotic surgical system 600 (e.g., for example, one piece) and may not be a separate component.

From the foregoing and with reference to the various figures, those skilled in the art will appreciate that certain modifications can be made to the disclosure without departing from the scope of the disclosure.

Although the description of computer-readable media contained herein refers to solid-state storage, it should be appreciated by those skilled in the art that computer-readable storage media can be any available media that can be accessed by the processor 30. That is, computer readable storage media may include non-transitory, volatile, and non-volatile, removable and non-removable media implemented in any method or technology for storage of information such as for example, computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the workstation 20.

What is claimed is:

1. A system, comprising:

a catheter including a camera configured to capture images of a patient's anatomy;

a biopsy tool; and a workstation operably coupled to the catheter and the biopsy tool, the workstation including a memory and a processor, the memory storing instructions, which when executed by the processor cause the processor to:

detect proximity of the catheter to target tissue within the patient's anatomy;

generate a radius extending from a center of the target tissue;

receive a plurality of images captured by the camera at a plurality of locations within extents of the generated radius in the patient's anatomy;

identify coordinates of the catheter at each respective location at which each received image of the plurality of images was captured;

identify coordinates of the biopsy tool within the patient's anatomy;

identify an image of the plurality of received images having coordinates corresponding to the identified coordinates of the biopsy tool; and display the identified image.

2. The system according to claim 1, further comprising an extended working channel configured to receive the catheter and the biopsy tool.

3. The system according to claim 2, further comprising the memory storing thereon further instructions, which when executed by the processor cause the processor to receive the plurality of images captured by the camera at the plurality of locations as the catheter is advanced within the patient's anatomy.

4. The system according to claim 2, further comprising the memory storing thereon further instructions, which when executed by the processor cause the processor to identify the coordinates of the biopsy tool within the patient's anatomy as the biopsy tool is advanced within a working channel of the catheter.

5. The system according to claim 1, further comprising the memory storing thereon further instructions, which when executed by the processor cause the processor to generate a 3-dimensional rendering of the patient's anatomy using the plurality of received images.

6. The system according to claim 1, further comprising the memory storing thereon further instructions, which when executed by the processor cause the processor to monitor coordinates of the biopsy tool in real-time as the biopsy tool is caused to be manipulated within the patient's anatomy.

7. The system according to claim 6, further comprising the memory storing thereon further instructions, which when executed by the processor cause the processor to update the displayed identified image in real-time corresponding to the manipulation of the biopsy tool within the patient's anatomy.

8. A system, comprising:

an extended working channel navigable within a patient's anatomy;

a catheter selectively receivable within the extended working channel, the catheter including a camera configured to capture images of a patient's anatomy;

a biopsy tool selectively receivable within the extended working channel; and a workstation operably coupled to the catheter and the biopsy tool, the workstation including a memory and a processor, the memory storing instructions, which when executed by the processor cause the processor to:

detect proximity of the catheter to target tissue within the patient's anatomy;

generate a radius extending from a center of the target tissue;

receive a plurality of images captured by the camera at a plurality of locations within extents of the generated radius in the patient's anatomy;

identify coordinates of the catheter at each respective location at which each received image of the plurality of images was captured;

generate, using the received plurality of images, a 3D representation of the patient's anatomy;

identify coordinates of the biopsy tool within the patient's anatomy;

identify a position within the generated 3D representation corresponding to the identified coordinates of the biopsy tool; and display the 3D representation from a perspective corresponding to the identified coordinates of the biopsy tool.

9. The system according to claim 8, further comprising the memory storing further instructions, which when executed by the processor cause the processor to monitor coordinates of the biopsy tool as the biopsy tool is manipulated within the patient's anatomy.

10. The system according to claim 9, further comprising the memory storing further instructions, which when executed by the processor cause the processor to update a displayed perspective of the 3D representation corresponding to the manipulation of the biopsy tool within the patient's anatomy.

11. A method of performing a surgical procedure, comprising:

detecting proximity of a catheter to target tissue within a patient's anatomy;

generating a radius extending from a center of the target tissue;

capturing a plurality of images at a plurality of locations within extents of the generated radius in the patient's anatomy, wherein the plurality of images is captured using a camera disposed on the catheter;

identifying coordinates of the catheter at each respective location at which each received image of the plurality of images was captured;

withdrawing the catheter from the patient's anatomy;

advancing a biopsy tool into the patient's anatomy;

identifying coordinates of the biopsy tool within the patient's anatomy;

identifying an image of the plurality of received images having coordinates corresponding to the identified coordinates of the biopsy tool; and displaying the identified image.

12. The method according to claim 11, wherein withdrawing the catheter from the patient's anatomy of the patient includes withdrawing the catheter from an extended working channel.

13. The method according to claim 11, further comprising monitoring coordinates of the biopsy tool as the biopsy tool is manipulated within the patient's anatomy.

14. The method according to claim 13, further comprising updating the displayed identified image corresponding to the manipulation of the biopsy tool within the patient's anatomy.

* * * * *